US007141616B2

(12) United States Patent
Hecht et al.

(10) Patent No.: US 7,141,616 B2
(45) Date of Patent: Nov. 28, 2006

(54) RADICALLY CURABLE URETHANE PREPOLYMERS AND THEIR USE IN DENTAL MATERIALS

(75) Inventors: Reinhold Hecht, Kaufering (DE); Günther Lechner, Wörthsee (DE); Thomas Lehmann, Burghausen (DE); Gunther Eckhardt, Bad Duerrenberg (DE); Bernd Gangnus, Andechs (DE)

(73) Assignee: 3M ESPE AG, Seefeld (DE)

( * ) Notice: Subject to any disclaimer, the term of this patent is extended or adjusted under 35 U.S.C. 154(b) by 179 days.

(21) Appl. No.: 10/149,607

(22) PCT Filed: Dec. 15, 2000

(86) PCT No.: PCT/EP00/12775

§ 371 (c)(1),
(2), (4) Date: Jun. 14, 2002

(87) PCT Pub. No.: WO01/44338

PCT Pub. Date: Jun. 21, 2001

(65) Prior Publication Data

US 2003/0008967 A1 Jan. 9, 2003

(30) Foreign Application Priority Data

Dec. 17, 1999 (DE) ................. 199 61 342

(51) Int. Cl.
*A61K 6/09* (2006.01)
*A61K 6/083* (2006.01)
*C08G 18/62* (2006.01)
*C08L 75/14* (2006.01)
*C08F 2/46* (2006.01)

(52) U.S. Cl. ............. 523/115; 433/80; 433/89; 433/212.1; 433/215; 433/218; 433/228.1; 522/90; 522/96; 522/98; 522/174; 523/116; 525/123; 525/127; 525/131; 525/454; 525/455; 528/49; 528/73; 528/75; 528/80; 560/25; 560/26; 560/115; 560/158

(58) Field of Classification Search ........... 523/115, 523/116; 522/90, 96, 98, 174; 525/123, 525/127, 131, 455, 454; 528/80, 49, 73, 528/75; 560/25, 26, 115, 158; 433/80, 89, 433/212.1, 215, 218, 228.1
See application file for complete search history.

(56) References Cited

U.S. PATENT DOCUMENTS

| | | | | |
|---|---|---|---|---|
| 3,066,112 A | | 11/1962 | Bowen et al. | 523/116 |
| 3,541,068 A | | 11/1970 | Taylor et al. | 523/116 |
| 4,206,205 A | | 6/1980 | Mrozik et al. | 424/180 |
| 5,096,938 A | | 3/1992 | Beck et al. | 522/100 |
| 5,334,420 A | * | 8/1994 | Hartung et al. | 427/407.1 |
| 5,990,245 A | * | 11/1999 | Esselborn et al. | 525/330.6 |
| 6,025,031 A | * | 2/2000 | Lettmann et al. | 427/388.4 |

FOREIGN PATENT DOCUMENTS

| | | |
|---|---|---|
| CA | 1297489 | 3/1992 |
| DE | 14 95 520 | 4/1969 |
| DE | 26 58 530 | 6/1978 |
| DE | 28 16 823 A1 | 10/1978 |
| DE | 28 16 823 C2 | 4/1982 |
| DE | 331 6592 | 11/1984 |
| DE | 370 4098 | 8/1988 |
| DE | 293 487 A5 | 9/1991 |
| DE | 404 0290 | 7/1992 |
| DE | 2 312 559 | 9/1993 |
| DE | 444 5266 | 6/1996 |
| DE | 19 92 82 38 | 12/2000 |
| EP | 0 007 508 | 2/1980 |
| EP | 0 007 508 A2 | 2/1980 |
| EP | 0 007 508 A3 | 2/1980 |
| EP | 0 047 902 | 3/1982 |
| EP | 0 047 902 A2 | 3/1982 |
| EP | 0 047 902 A3 | 3/1982 |
| EP | 0 057 474 | 8/1982 |
| EP | 0 057 474 A2 | 8/1982 |
| EP | 0 057 474 A3 | 8/1982 |
| EP | 0 059 451 | 9/1982 |
| EP | 0 059 451 A1 | 9/1982 |
| EP | 0 073 413 | 3/1983 |
| EP | 0 073 413 A2 | 3/1983 |
| EP | 0 073 413 A3 | 3/1983 |
| EP | 0 184 095 | 6/1986 |
| EP | 0 184 095 A2 | 6/1986 |
| EP | 0 205 846 A1 | 12/1986 |

(Continued)

OTHER PUBLICATIONS

Knebelkamp et al., α, ω-Polymethacrlyatdiole in PUR-Bindemitteln, Sonderdruck aus FARBE & LACK 2/99, Seiten 24-29, Vincentz Verlag, Hanonver, Germany [including English Language abstract: "7, 7-Polymethacylate diols in PUR binders," European Coatings Journal, 1999; 9:52-58.] (6Pgs total).

(Continued)

*Primary Examiner*—Rabon Sergent
(74) *Attorney, Agent, or Firm*—Mueting, Raasch & Gebhardt, P.A.

(57) ABSTRACT

The invention relates to urethane prepolymers, obtainable by reaction of:
 (A) 15 to 85 wt.-% of one or more α,ω-terminated poly(meth)acrylate diols,
 (B) 0 to 30 wt.-% of one or more radically curable, polyhydroxy-functional compounds,
 (C) 14 to 60 wt.-% of one or more polyisocyanates,
 (D) 1 to 40 wt.-% of a monofunctional compound, reactive vis-à-vis isocyanate groups, which also contains one or more radically curable grouping,
as well as their use.

19 Claims, No Drawings

FOREIGN PATENT DOCUMENTS

| | | |
|---|---|---|
| EP | 0 205 846 B1 | 12/1986 |
| EP | 0 257 777 A2 | 3/1988 |
| EP | 0 374 824 A2 | 6/1990 |
| EP | 0 374 824 A3 | 6/1990 |
| EP | 0 374 824 B1 | 6/1990 |
| EP | 0 460 478 A2 | 12/1991 |
| EP | 0 622 378 | 11/1994 |
| EP | 0 622 378 B1 | 9/1997 |
| EP | 0 945 469 A1 | 9/1999 |
| GB | 1 576 080 | 10/1980 |
| WO | 97/42247 * | 11/1997 |
| WO | WO 00 78271 | 12/2000 |

OTHER PUBLICATIONS

*Product data sheet (i.e. sales or company literature)*: "TEGO® Diol BD 1000 TEGO® Diol MD 1000 N TEGO® Diol MD 1000 X" datasheet. Tego Chemie Service GmbH, Gerlingstrasse 64, Essen Germany (Available before Apr. 1999) (4 pgs in German, 1 pg in English).

*U.V. and E.B. Curing Formulation for Printing Inks, Coatings and Paints*, Holman and Oldring (Eds.), SITA Technology, London, England, Title page, Publication page, Table of Contents, and pp. 36-46 (18pgs total).

*Volume II Prepolymers & Reactive Diluents Chemistry & Technology of UV & EB Formulation for Coatings, Inks & Paints*, Webster (Ed.), John Wiley & Sons and SITA Technology Ltd., London, UK, Title page, Publication page, Table of Contents, and pp. 35-41. (13 pgs total).

Knebelkamp et al., "α, ω-Polymethacrylate diols in PUR Binders, New components for the modificatin of resin binders," Special Edition from *Farbe & Lack*, 2/99, pp. 24-29, Vincentz Publishing Co., Hanover, Germany (English Translation, 8 pgs.).

Reusmann et al., "α, ω-Polymethacrylate diols in PUR Binders," European Coatings Journal, Sep. 1999, 263-266 (4pgs.).

*Product data sheet (i.e. sales or company literature)*: "TEGO® Diol BD 1000 TEGO® Dilo MD 1000 N TEGO® Diol MD 1000 X" datasheet. Tego Chemie Service GmbH, Gerlingstrasse 64, Essen Germany (Available before Apr. 1999) (Translation in English, 5 pgs.).

DIN EN ISO 11909, "Binders for paints and varnishes Polyisocyanate resins General methods of test (ISO 11909:1996) English version of DIN EN ISO 11909," Dec. 1998, 3 pgs.

EN ISO 11909, "English version Binders for paints and varnishes Polyisocyanate resins General methods of test (ISO 11909:1996)," Apr. 1998, 6 pgs.

DIN 53240, "German Standards Determination of the hydroxil value," Dec. 1971, 7 pgs.

* cited by examiner

RADICALLY CURABLE URETHANE PREPOLYMERS AND THEIR USE IN DENTAL MATERIALS

This application is the national phase under 35 U.S.C. § 371 of PCT International Application No. PCT/EP00/12775 which has an International filing date of Dec. 15, 2000, which designated the United States of America.

The present invention describes di- or higher-functional radically curable urethane prepolymers and their use in polymerizable compounds. The invention furthermore describes the use of the polymerizable compounds in the dental field, for example as filling materials, stump build-up materials, fixing cements, temporary crown and bridge materials, dental materials, modelling materials or for the preparation of inlays, onlays, facing shells, crowns and bridges.

Materials suitable for such purposes advantageously display a high impact strength, high elasticity with high hardness as well as a small tendency to swell. These properties are largely determined by the monomers used.

In the state of the art, above all, ethylenically unsaturated compounds such as acrylic acid and/or methacrylic acid esters are described as suitable monomers.

In the dental industry, essentially 7,7,9-trimethyl-4,13-dioxo-3,14-dioxa-5,12-diazahexadecane-1,16-dioxy-dimethacrylate (e.g. Plex 666-1, Röhm) for example is used in particular from the group of the urethane(meth)acrylates, which with its low molecular weight has little elastifying effect and improves the impact strength only slightly.

To improve the elastifying properties and the impact strength, in the lacquer industry for example, a variety of polyurethane oligomers end-functionalized with (meth)acrylate groups which have polyester, polyether, polybutadiene and/or polycarbonate units are used with radically curable systems. However, these systems have a range of disadvantages:

Thus the ester bonds of the polyester urethane(meth)acrylates and of the polycarbonate urethane(meth)acrylates tend towards hydrolysis upon contact with moisture, whereby in particular the mechanical values of formulations prepared therefrom are reduced.

Polyether-based urethane(meth)acrylates show a clearly lower susceptibility to hydrolysis. However, these systems, due to their hydrophilicity, display an increased water absorption and thus an increased tendency to swell and lower strength, which involves a readiness to discolour. Such systems are therefore not suitable for aesthetically demanding applications.

A further disadvantage of the polyether urethane(meth)acrylates lies in their lack of resistance to oxidation as a result of the degradation of the oxidative polyether chain.

Although the polybutadiene urethane(meth)acrylates show excellent elastic properties, they are readily discoloured by the double bonds present through short-wave radiation as contained in sunlight.

In principle, urethane(meth)acrylates can also be prepared from low-molecular aliphatic and/or aromatic diols. However, these do not show elastic and impact strength-modifying properties as good as those of the above-named urethane(meth)acrylates which contain soft segments on polyester, polyether, polybutadiene and/or polycarbonate units.

There is therefore a substantial demand for monomers which in curable compounds lead to an improvement in impact strength, good elasticity with high hardness and swell only slightly.

The object of the present invention is to provide monomers from which compounds can be formulated which display an improved impact strength with simultaneous high hardness and good elasticity.

Surprisingly, it was found that these requirements are met with urethane prepolymers which can be obtained by reaction of:

(A) 15 to 85 wt.-%, preferably 20 to 80 wt.-% of one or more α,ω-terminated poly(meth)acrylate diols, (B) 0 to 30 wt.-%, preferably 0 to 20 wt.-% of one or more radically curable, polyhydroxy-functional compounds, (C) 14 to 60 wt.-%, preferably 18 to 50 wt.-% of one or more polyisocyanates, (D) 1 to 40 wt.-%, preferably 2 to 35 wt.-% of a monofunctional compound reactive vis-à-vis isocyanate groups, which also contains one or more radically curable groupings.

Surprisingly, compounds which were formulated with the monomers according to the invention show an extremely small degree of swelling.

Furthermore, the monomers are toxicologically acceptable and are therefore suitable in particular for use in the dental field.

The α,ω-terminated poly(meth)acrylate diols of the component (A) are compounds which contain two terminal hydroxyl groups. Suitable starting compounds for building up these α,ω-terminated poly(meth)acrylate diols and the preparation process for these compounds are described in detail in EP-B1-1-0 622 378 and EP-B1-0 205 846. In particular, an α,ω-terminated poly(meth)acrylate diol useful in the present invention is one of the general formula

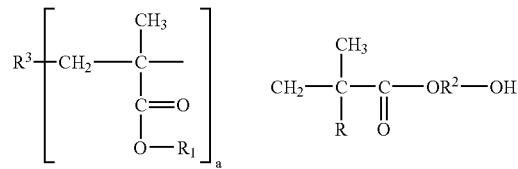

where $R^1$ is a halogenated or whalogenated alkyl radical having from 1 to 10 carbons atoms, $R^2$ is
(1) a divalent aliphatic, saturated or unsaturated hydrocarbon radical having from 2 to 20 carbon atoms, a cycloaliphatic hydrocarbon radical having from 5 to 10 carbon atoms or an aliphaticaromatic hydrocarbon radical having from 8 to 20 carbon atoms,
(2) a divalent aliphatic ether radical $-R^5-O-R^6-$, whose radicals R5 and R6 together have from 4 to 20 carbon atoms, or
(3) a polyether radical of the general formula $-(C_nH_{2n}O)_m-C_pH_{2p}-$, where the index n has a value from 2 to 4, the index m has a value of $\geq 1$ and the index p has a value of 2, 3 or 4, $R^3$ is the radical $-S-CH_2CH_2-OH$, $-S-CH_2CH_2CH_2CH_2-OH$, $-S-CH_2CH_2CH_2CH_2CH_2CH_2-OH$ or $-S-CH_2-C_6H_4-CH_2OH$ and a has a value of $\geq 4$.

The low-molecular-weight (meth)acrylate polymers containing essentially α,ω-terminal hydroxyl groups and having an hydroxyl equivalent weight of from 500 to 5000, that are useful in the present invention are made by a process in which, in each case based on the monomer mixture, from 10 to 100% by weight of an alkyl methacrylate having 1 to 14 carbon atoms in the alkyl radical and/or from 0 to 100% by weight of an alkyl acrylate having 2 to 14 carbon atoms in the alkyl radical and from 0 to 40% by weight of a monomer which can be copolymerized with the methacrylate or acrylate are subjected to free-radical polymerization. The free-radical polymerization is performed in the presence of an initiator from the group comprising hydroxyl group-containing peroxides, hydroperoxides or hydroxyl group-containing azo compounds which is capable of transferring hydroxyl groups onto the polymer molecule, and in the presence of a redox compound as accelerator with hydroxyl group-containing regulators of the general formula $$HO\text{-}A\text{-}S_x\text{-}B\text{-}OH_1 \qquad (I)$$

in which A and B are each a divalent organic radical, and $x \geq 2$.

The component (B) is radically curable compounds, for example (meth)acrylate-based, which in accordance with DIN 53 240 display OH numbers preferably from 40 to 700 mg KOH/g and particularly preferably from 80 to 500 mg KOH/g.

Suitable representatives are for example polyhydroxy-group-containing polyester(meth)acrylate prepolymers as described in U.S. Pat. No. 4,206,205, DE-OS40 40 290, DE-OS-33 16 592, DE-OS-37 04 098 and in "UV & EB Curing Formulations for Printing Inks Coatings and Paints", ed R. Holman and P. Oldring, published by SITA Technology, London (England) 1988, p 36 ff.

Alternatively, polyhydroxy-group-containing polyepoxy (meth)acrylate prepolymers which are accessible by reaction of polyepoxides with (meth)acrylic acid, and/or polyhydroxy-group-containing polyurethane(meth)acrylate prepolymers can also be used.

Particularly preferred representatives are polyhydroxy-group-containing polyepoxy(meth)acrylate prepolymers, such as 2,2-bis[p-(2'-hydroxy-3'-methacryloyloxypropoxy)-phenyl]-propane (bis-GMA) or 2,2-bis-[p-(2'hydroxy-3'-acryloyloxypropoxy)-phenyl]-propane (bis-GA) and polyhydroxy-group-containing (meth)acrylate esters such as glycerol mono(meth)acrylate, trimethylolpropane mono (meth)acrylate or pentaerythritol di(meth)acrylate.

Suitable polyisocyanates of the component (C) are of an aliphatic, cycloaliphatic and/or aromatic nature and contain at least two free isocyanate groups. Preferably, diisocyanates $X(NCO)_2$ are used, X representing an aliphatic hydrocarbon radical with 2 to 12 C atoms, a cycloaliphatic hydrocarbon radical with 5 to 18 C atoms, an aromatic hydrocarbon radical with 6 to 16 C atoms and/or an araliphatic hydrocarbon radical with 7 to 15 C atoms.

Examples of such diisocyanates are: 1,4-tetramethylene diisocycanate, 1,6-hexamethylene diisocycanate (HDI), 2,4,4-trimethyl-hexamethylene diisocycanate, isophorone diisocycanate, 4,4'-dicyclohexylmethane diisocycanate, meta- and para-tetramethylxylene diisocycanate, 1,4-phenylene diisocycanate, 2,6- and 2,4-toluene diisocycanate, 1,5-naphthylene diisocycanate, 2,4' and 4,4'-diphenylmethane diisocycanate.

It is naturally also possible to use, or also use a proportion of, the higher-functional polyisocyanates known from polyurethane chemistry or else modified polyisocyanates, for example containing carbodiimide groups, allophanate groups, isocyanurate groups and/or biuret groups. Particularly preferred isocyanates are isophorone diisocyanate and 2,4,4-trimethyl-hexamethylene diisocyanate.

Compounds of the component (D) contain a functional group which is reactive vis-à-vis isocyanates, for example a hydroxy group or amino group, and also have one or more radically curable groupings. The radically curable groupings are preferably (meth)acrylate-based. The representatives of this component (D) can also be used as a mixture.

Suitable representatives are for example 2-hydroxy(meth) acrylate, 2-hydroxypropyl (meth)acrylate, glycerol di(meth) acrylate and/or trimethylolpropane di(meth)acrylate. Particularly preferred are 2-hydroxyethyl methacrylate (HEMA) and/or 2-hydroxyethyl acrylate (HEA).

For the preparation of the urethane prepolymers according to the invention, for example the components (A) to (C) are introduced first into a reactor or fed individually in metered quantities and converted to an NCO-containing prepolymer under anhydrous conditions, for example in a temperature range from −20° C. to 160° C., preferably in a temperature range from 0° C. to 130° C. and particularly preferably a temperature range from 20° C. to 100° C.

The equivalence ratio of isocyanate groups to compounds reactive vis-à-vis isocyanate groups is 1.1:1 to 8:1, preferably 1.5:1 to 4:1.

The isocyanate polyaddition reaction can take place in the presence of catalysts known from polyurethane chemistry, for example organotin compounds such as dibutyltin dilaurate or amine catalysts such as diazabicyclo[2.2.2]octane. Furthermore, the synthesis can take place both in the melt and in a suitable solvent which can be added before or during the prepolymer preparation. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

Measured doses of the component (D) are added complete or portionwise to the NCO-containing prepolymers accompanied by stirring and reacted for example in a temperature range from −20° C. to 160° C., preferably in a temperature range from 0° C. to 130° C. and particularly preferably a temperature range from 20° C. to 100° C. The quantity of component (D) to be used depends on the still present unreacted isocyanate groups of the prepolymer. The measurement of the isocyanate content of the prepolymer takes place for example according to DIN 53 185.

For example, the average by weight of the molecular weight ($M_W$) obtained from GPC measurements against polystyrene standards can lie between 400 and 200,000 g/mol, preferably between 500 and 100,000 g/mol and particularly preferably between 600 and 50,000 g/mol. Naturally, the molecular weights can also lie outside these ranges provided it allows the use of the polyurethane prepolymers according to the invention.

The urethane prepolymers according to the invention are suitable for example for the preparation of curable compounds such as dental compounds or for coating, pouring and gluing of substrates.

Curable formulations, for example for use in the dental field, preferably contain the following components:

(C1) 1 to 70 wt.-%, in particular 2 to 50 wt.-% of urethane prepolymer according to the invention, (C2) 8.9 to 70 wt.-%, in particular 10 to 60 wt.-% of one or more radically polymerizable monomers, (C3) 10 to 90 wt.-%, in particular 10 to 87.9 wt.-% fillers, (C4) 0.1 to 5 wt.-%, in particular 0.1 to 3 wt.-% initiators and optionally activators, (C5) 0 to 30 wt.-%, in particular 0 to 20 wt.-% additives, optionally pigments, thixotropic auxiliaries, plasticizers.

The compounds formulated with the urethane prepolymers according to the invention are characterized by particularly good impact strength, good elasticity with high hardness and a surprisingly small tendency to swell.

As component (C2) are used mono-, di- or higher-functional ethylenically unsaturated compounds, preferably acrylate- and/or methacrylate-based. These can contain both monomeric and higher-molecular oligomeric or polymeric acrylates. Furthermore, they can be used alone or in mixture in the formulations.

Suitable monomers are for example the acrylic acid and methacrylic acid esters of mono-, di- or higher-functional alcohols. As examples there can be named: methyl (meth) acrylate, iso-butyl (meth)acrylate, ethylene glycol di(meth) acrylate, triethylene glycol di(meth)acrylate (TEGDMA), hexanediol di(meth)acrylate, dodecanediol di(meth)acrylate and trimethylolpropane tri(meth)acrylate.

Also advantageously usable is bisphenol-A di(meth)acrylate as well as the ethoxy- or propoxylated di(meth)acrylates derived therefrom. The monomers described in U.S. Pat. No. 3,066,112 based on bisphenol-A and glycidyl(meth)acrylate or their derivatives resulting from the addition of isocyanates are also suitable.

Particularly suitable are also the diacrylic and dimethacrylic acid esters of bis(hydroxymethyl)-tricyclo[$5.2.1.0^{2.6}$]-decane named in DE-C-28 16 823 and the diacrylic and dimethacrylic acid esters of the compounds of bis(hydroxymethyl)-tricyclo[$5.2.1.0^{2.6}$]-decane extended by 1 to 3 ethylene oxide and/or propylene oxide units.

Urethane(meth)acrylates, such as 7,7,9-trimethyl-4,13-dioxo-5,12-diazahexadecane-1,16-dioxy-dimethacrylate (UDMA), can also be a constituent of the component (C2).

Fillers according to component (C3) can be inorganic fillers, for example quartz, ground glasses, non-water-soluble fluorides such as $CaF_2$, silica gels such as silicic acid, in particular pyrogenic silicic acid and granulates thereof. Cristobalite, calcium silicate, zirconium silicate, zeolites, including the molecular sieves, metal oxide powders, such as aluminium or zinc oxides or their mixed oxides, barium sulphate, yttrium fluoride, calcium carbonate can also be used as fillers.

Fluoride-releasing fillers, for example complex inorganic fluorides of the general formula $A_nMF_m$ as described in DE-A-44 45 266, can be used or added. A represents a mono- or polyvalent cation, M a metal of the IIIrd, IVth, Vth main or sub-group, n an integer from 1 to 3 and m an integer from 4 to 6.

Organic fillers can also be a constituent of the component (C3). As examples there can be named customary methyl methacrylate-based bead polymers and copolymers, which can be obtained for example from Röhm under the name "Plexidon" or "Plex".

For better incorporation into the polymer matrix, it can be advantageous to hydrophobize the named fillers and, if present, X-ray-opaque additives. The quantity of silane used is usually 0.5 to 10 wt.-% relative to inorganic fillers, preferably 1 to 6 wt.-%, quite particularly preferably 2 to 5 wt.-% relative to inorganic fillers. Customary hydrophobing agents are silanes, for example trimethoxymethacryloxypropyl silane. The maximum average particle size of the inorganic fillers is preferably 15 µm, in particular 8 µm. Fillers with an average particle size of <3 µm are quite particularly preferably used.

By initiators according to component (C4) are meant initiator systems which effect the radical polymerization of the monomers, for example photoinitiators and/or so-called redox-initiator systems and/or thermal initiators.

Suitable as photoinitiators are for example α-diketones such as camphorquinone, in combination with secondary and tertiary amines, or mono- and bisacylphosphinic oxides such as 2,4,6-trimethylbenzoyldiphenyl-phosphinic oxide and bis-(2,6-dichlorobenzoyl)-4-n-propylphenyl-phosphinic oxide. However, other compounds of this type as described in European patent publications EP-A-0 073 413, EP-A-0 007 508, EP-A-0 047 902, EP-A-0 057 474 and EP-A-0 184 095 are also suitable.

Organic peroxide compounds together with so-called activators are suitable as redox initiator systems. In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines known from DE-A-26 58 530, in particular N,N-bis-(β-oxybutyl)-3,5-di-t-butylaniline as well as N,N-bis-(hydroxyalkyl)-3,4,5-trimethylaniline.

Well-suited activators are also the barbituric acids and barbituric acid derivatives described in DE-B-14 95 520 as well as the malonyl sulfamides described in EP-A-0 059 451. Preferred malonyl sulfamides are 2,6-dimethyl-4-isobutylmalonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide.

For further acceleration, the polymerization is in this case preferably carried out in the presence of heavy-metal compounds and ionogenic halogen or pseudohalogen. Copper is particularly suitable as heavy metal, chloride ion as halide. The heavy metal is suitably used in the form of soluble organic compounds. Likewise, the halide and pseudohalide ions are suitably used in the form of soluble salts, as examples there can be named the soluble amine hydrochlorides as well as quarternary ammonium chloride compounds.

If the dental compounds according to the invention contain a redox initiator system comprising organic peroxide and activator, peroxide and activator are preferably present in parts of the dental compound according to the invention physically separated from one another and are homogeneously mixed together only immediately before use. If organic peroxide, copper compound, halide and malonyl sulfamide and/or barbituric acid are present next to each other, it is particularly useful for the organic peroxide, malonyl sulfamide and/or barbituric acid and the combination of copper compound/halide to be present in three constituents physically separated from one another. For example, the combination of copper compound/halide, polymerizable monomers and fillers can be kneaded to a paste and the other components kneaded to two separate pastes in the above-described manner each with a small quantity of fillers or in particular thixotropic auxiliaries, such as silanized silicic acid, and a plasticizer, for example phthalate. On the other hand, the polymerizable monomers can also be present together with organic peroxide and fillers. Alternatively, a distribution of organic peroxide, copper compound, halide and malonyl sulfamide and/or barbituric acid can be realized according to DE-A-199 28 238.

As representatives of the component (C5), soluble organic polymers can for example be used to increase the flexibility of the compounds. Suitable are for example polyvinyl acetate as well as copolymers based on vinyl chloride/vinyl acetate, vinyl chloride/vinyl isobutyl ether and vinyl acetate/ maleic acid dibutyl ether. Well-suited as additional plasticizers are for example dibutyl, dioctyl and dinonyl phthalates or adipates as well as higher-molecular polyphthalic acid and adipic acid esters. There can also be used as thixotropic auxiliaries, in addition to pyrogenic silicic acids, modified layered silicates (bentonites) or organic modifiers, for example on the basis of hydrogenated castor oils.

Furthermore, retardants as described in EP-A-0 374 824 as component (d) can also be contained as additives in the formulations.

The components according to the invention can be distributed for example over two pastes as follows:
Paste 1: Parts of C3, parts of C4, C5
Paste 2: C1, C2, parts of C3, parts of C4.

Dental materials which contain the urethane prepolymers according to the invention can be used for example as filling materials, cements, temporary crown and bridge materials, facing plastics, prosthesis materials, orthodontic materials, plastics for fissure sealing, modelling plastics or model plastics.

The urethane prepolymers according to the invention and formulations prepared therefrom are also suitable for the gluing and coating of substrates. As examples can be named the coating of wood, metal, glass or plastic. Furthermore, the urethane prepolymers according to the invention and formulations prepared therefrom are also suitable for the preparation of moulded bodies.

Preferably, compounds containing the urethane prepolymers according to the invention are formulated as two-component mixtures, these preferably being packed into a cartouche system and the compounds applied via a static or dynamic mixing set, homogeneously mixed and cured.

In the following, the invention is explained in more detail by means of examples, the latter not to be seen as limiting the invention in any way.

EXAMPLES

Preparation Example 1

Urethane Acrylate 212 g (approx. 0.2 mol) Tego-Diol BD-1000, 70 g ethyl acetate and 0.1 g dibutyltin dilaurate are introduced into a 2 l 3-neck flask equipped with thermometer, reflux cooler, mechanical stirrer and drying tube, and 126 g (0.6 mol) trimethyl-hexamethylene diisocyanate added in measured doses, accompanied by cooling, over a period of 30 minutes. The reaction mixture is stirred for 20 hours at room temperature until the isocyanate content has fallen to 7.7%. 91 g hydroxyethylacrylate is added accompanied by cooling. After 72 hours at room temperature, an isocyanate value of 0 is recorded, at which the reaction is ended. The ethyl acetate can be distilled off in fine vacuum.

Preparation Example 2

Urethane Methacrylate 212 g (approx. 0.2 mol) Tego-Diol BD-1000, 140 g acetone and 0.1 g dibutyltin dilaurate are introduced first into a 2l 3-neck flask equipped with thermometer, reflux cooler, mechanical stirrer and drying tube, and 84 g (0.4 mol) trimethyl-hexamethylene diisocyanate added in measured does, accompanied by cooling, over a period of 30 minutes. The reaction mixture is stirred for 20 hours at room temperature until the isocyanate content has fallen to 3.7%. 53 g hydroxyethyl methacrylate is added, accompanied by cooling. After 72 hours at room temperature, an isocyanate value of 0.1 is recorded, at which the reaction is ended. The ethyl acetate can be distilled off in fine vacuum.

Application Examples 10 g catalyst and 100 g base paste each are kneaded from the constituents listed in Table 1 and Table 2. These are packed into 10:1 cartouches from Mixpack, Rotkreuz. To apply them, they are pressed through a static mixing device by means of a dispenser and mixed, so that curing occurs within several minutes.

TABLE 1

| Catalyst | | | |
|---|---|---|---|
| Component | Constituent | Quantity [g] | Wt.-% |
| C3 | Fluoroaluminosilicate glass powder ($\phi$ < 12 µm) | 3.4 | 34 |
| C3 | Silanized microfine silicic acid (HDKH 2000, Wacker, Burghausen) | 0.7 | 7 |
| C4 | 1-benzyl-5-phenyl barbituric acid | 0.1 | 1 |
| C4 | 3,5,5-trimethylhexanoic acid tertiary butyl ester | 0.06 | 0.6 |
| C5 | 2,2-bis-4-(2-hydroxyethoxyphenyl)-propane-bis-acetate | 5.74 | 57.4 |

TABLE 2

| Component | | Quantity [g] | Wt.-% |
|---|---|---|---|
| Application example 1 | | | |
| Base 1 | | | |
| C3 | Fluoroaluminosilicate glass powder ($\phi$ < 12 µm) silanized with methacryloxypropyl trimethoxy silane | 25 | 25 |
| C3 | Silanized microfine silicic acid (HDKH 2000, Wacker) | 7 | 7 |
| C4 | Bis(1-phenylpentane-1,3-dionato)-copper(II) | 0.00775 | 0.00775 |
| C4 | (β-phenylethyl)-dibutyl-ammonium-chloride | 0.352 | 0.352 |
| C1 | Urethane acrylate: Preparation example 1 | 13.6 | 13.6 |
| C2 | 2,2-bis-4(acryloxy-bisethylene glycol)-phenylpropane | 54.04025 | 54.04025 |
| Application example 2 | | | |
| Base 2 | | | |
| C3 | Fluoroaluminosilicate glass powder ($\phi$ < 12 µm) silanized with methacryloxypropyl trimethoxy silane | 25 | 25 |
| C3 | Silanized microfine silicic acid (HDKH 2000, Wacker) | 7 | 7 |

TABLE 2-continued

| | | Quantity [g] | Wt.-% |
|---|---|---|---|
| C4 | Bis-(1-phenylpentane-1,3-dionato)-copper(II) | 0.00775 | 0.00775 |
| C4 | (β-phenylethyl)-dibutyl-ammonium-chloride | 0.352 | 0.352 |
| C1 | Urethane methacrylate: Preparation example 2 | 13.6 | 13.6 |
| C2 | 2,2-bis(4-acryloxy-bisethylene glycol)-phenylpropane | 54.04025 | 54.04025 |

| | Quantity [g] | Wt.-% |
|---|---|---|
| Comparison example 1 | | |
| Base 3 | | |
| Fluoroaluminosilicate glass powder (φ < 12 μm) silanized with methacryloxypropyl trimethoxy silane | 25 | 25 |
| Silanized microfine silicic acid (HDKH 2000, Wacker) | 7 | 7 |
| Bis(1-phenylpentane-1,3-dionato)-copper(II) | 0.00775 | 0.00775 |
| (β-phenylethyl)-dibutyl-ammonium-chloride | 0.352 | 0.352 |
| Polyesterurethane-acrylate 98-446 (Rahn) | 13.6 | 13.6 |
| 2,2-bis-4(acryloxy-bisethylene glycol)-phenylpropane | 54.04025 | 54.04025 |
| Comparison example 2 | | |
| Base 4 | | |
| Fluoroaluminosilicate glass powder (φ < 12 μm) silanized with methacryloxypropyl trimethoxy silane | 25 | 25 |
| Silanized microfine silicic acid (HDKH 2000, Wacker) | 7 | 7 |
| Bis-(1-phenylpentane-1,3-dionato)-copper(II) | 0.00775 | 0.00775 |
| (β-phenylethyl)-dibutyl-ammonium-chloride | 0.352 | 0.352 |
| Polyesterurethane-acrylate BR-372 (Bomar) | 13.6 | 13.6 |
| 2,2-bis-4(acryloxy-bisethylene glycol)-phenylpropane | 54.04025 | 54.04025 |

The following measurement values were obtained with the cured testpieces:

TABLE 3

| Base | Polyurethane (meth) acrylate | Linear swelling, 7d in 36° C. $H_2O$ [%] | E-modulus [Mpa] | Bending on fracture [mm] | Impact strength [kJ/m$^2$] |
|---|---|---|---|---|---|
| 1 | Urethane acrylate: Preparation example 1 | 0.2 | 1450 | 1.7 | 9.41 |
| 2 | Urethane methacrylate: Preparation example 2 | 0.25 | 1200 | 1.3 | 9.97 |
| 3 | Polyester-urethane-acrylate 98-446 (Rahn) | 0.35 | 900 | 1.4 | 4.89 |
| 4 | Polyether-urethane-acrylate BR-372 (Bomar) | 0.4 | 1000 | 1.2 | 4.42 |

Measurement methods:
E-modulus and bending: 3-point bending test; Impact strength = Notched impact strength; Linear swelling after storage of testpieces for 7 days in water at 36° C.; figure as % of the starting length.

The testpieces prepared with the base pastes 3 and 4 not according to the invention display an increased swelling, a reduced E-modulus and a much reduced impact strength compared with the testpieces made from pastes according to the invention (base 1 and 2).

The invention claimed is:

1. A radically curable urethane prepolymer, obtained by reaction of:
   (A) 15 to 85 wt % of one or more α, ω-terminated poly(meth)acrylate diols,
   (B) 0 to 30 wt % of one or more radically curable, polyhydroxy-functional compounds,
   (C) 14 to 60 wt % of one or more polyisocyanates,
   (D) 1 to 40 wt % of a monofunctional compound, reactive with isocyanate groups, which also comprises one or more radically curable groupings, wherein the weight percentage is of the total reaction mixture, and further wherein the radically curable urethane prepolymer contains a di- or higher radically curable functionality.

2. The radically curable urethane prepolymer according to claim 1, wherein component (B) is present, and in which the component (B) exhibits an OH number from 40 to 700 mg KOH/g.

3. The radically curable urethane prepolymer according to claim 1, in which the component B, is present and is selected from the group consisting of polyhydroxy-group-containing polyester(meth)acrylate prepolymers, polyhydroxy-group-containing polyepoxy(meth)acrylate prepolymers and polyhydroxy-group-containing polyurethane(meth)acrylate prepolymers.

4. The radically curable urethane prepolymer according to claim 1, in which the component (C) is an aliphatic, cycloaliphatic or aromatic compound having at least two free isocyanate groups.

5. The radically curable urethane prepolymer according to claim 2, in which the component (C) is an aliphatic, cycloaliphatic or aromatic compound having at least two free isocyanate groups.

6. The radically curable urethane prepolymer of claim 1, in which the component (C) is at least one diisocyanate $X(NCO)_2$, X being selected from the group consisting of an aliphatic hydrocarbon radical with 2 to 12 C atoms, a cycloaliphatic hydrocarbon radical with 5 to 18 C atoms, an aromatic hydrocarbon radical with 6 to 16 C atoms and an araliphatic hydrocarbon radical with 7 to 15 C atoms.

7. The radically curable urethane prepolymer of claim 2, in which the component (C) is at least one diisocyanate $X(NCO)_2$, X being selected from the group consisting of an aliphatic hydrocarbon radical with 2 to 12 C atoms, a cycloaliphatic hydrocarbon radical with 5 to 18 C atoms, an aromatic hydrocarbon radical with 6 to 16 C atoms and an araliphatic hydrocarbon radical with 7 to 15 C atoms.

8. The radically curable urethane prepolymer of claim 3, in which the component (C) is at least one diisocyanate $X(NCO)_2$, X being selected from the group consisting of an aliphatic hydrocarbon radical with 2 to 12 C atoms, a cycloaliphatic hydrocarbon radical with 5 to 18 C atoms, an aromatic hydrocarbon radical with 6 to 16 C atoms and an araliphatic hydrocarbon radical with 7 to 15 C atoms.

9. The radically curable urethane prepolymer of any one of claims 1 to 8, in which the component (D) comprises a hydroxy group and, as a radically curable group, at least one (meth)acrylate group.

10. A composition comprising:
(C1) 1 to 70 wt % of at least one radically curable urethane prepolymer according to claim 1,
(C2) 8.9 to 70 wt % of one or more radically polymerizable monomers,
(C3) 10 to 90 wt % of at least one filler,
(C4) 0.1 to 5 wt % of at least one initiator, and optionally at least one activator,
(C5) 0 to 30 wt % of one or more additives, and optionally pigments, thixotropic auxiliaries and plasticizers;
in which the wt % is a percentage of the total weight of the composition.

11. The composition according to claim 10, in which component (C2) comprises at least one mono-, di- and/or higher-functional acrylic acid ester, at least one mono-, di- and/or higher-functional methacrylic acid ester, or both.

12. The composition according to claim 11, in which the acrylic acid ester, methacrylic acid ester or both comprise monomeric, oligomeric or polymeric acrylates, or a mixture thereof.

13. A kit for the preparation of dental materials comprising at least one cartouche with at least two chambers filled with a composition according to one of claims 10 to 12, and optionally including an applicator for the dispensing of dental materials, and/or optionally including a static mixing set.

14. A composition according to one of claims 10 to 12 that has been cured.

15. An applicator, comprising at least one cartouche that contains a composition according to one of claims 10 to 12.

16. A method for making a dental filling material, stump build-up material, fixing cement, temporary dental crown material, temporary dental bridge material, dental material, model material, inlay, onlay, facing shell, dental crown or dental bridge comprising polymerizing a composition according to claim 10.

17. A method for making a dental filling material, stump build-up material, fixing cement, temporary dental crown material, temporary dental bridge material, dental material, model material, inlay, onlay, facing shell, dental crown or dental bridge comprising mixing a radically curable urethane prepolymer according to claim 1 with at least one of:
a) at least one radically polymerizable monomer,
b) at least one filler,
c) at least one initiator, and optionally at least one activator, and
of one or more additives, and optionally pigments, thixotropic auxiliaries and plasticizers, and polymerizing the mixture.

18. A method for gluing or coating a substrate comprising applying the prepolymer of claim 1 to the substrate and polymerizing the prepolymer.

19. A method for preparing a molded article comprising filling a mold with the prepolymer of claim 1 and polymerizing the prepolymer.

* * * * *

UNITED STATES PATENT AND TRADEMARK OFFICE
CERTIFICATE OF CORRECTION

| | | |
|---|---|---|
| PATENT NO. | : 7,141,616 B2 | |
| APPLICATION NO. | : 10/149607 | |
| DATED | : November 28, 2006 | |
| INVENTOR(S) | : Hecht et al. | |

It is certified that error appears in the above-identified patent and that said Letters Patent is hereby corrected as shown below:

Title Page; item (56);

In Foreign Patent Documents, insert --EP 0 184 095 A3 6/1986--;

In the Abstract, item (57); delete "grouping" and insert --groupings--;

In column 2, line 29, delete "EP-B1-1-0 622 378" and insert --EP-B1-0 622 378--;

In column 3, line 27, delete "DE-OS40 40 290" and insert --DE-OS-40 40 290--;

In column 6, line 32, delete "2,6-dibutyl4-propylmalonyl sulfamide" and insert --2,6-dibutyl-4-propylmalonyl sulfamide--;

In column 6, line 32, delete "2,6-dimethyl4-ethylmalonyl" and insert --2,6-dimethyl-4-ethylmalonyl--;

In column 6, line 33, delete "2,6-dioctyl4-isobutyl malonyl" and insert --2,6-dioctyl-4-isobutylmalonyl--;

In column 9, Table 2, component, C2, delete "2,2-bis(4-acryloxybisethylene glycol)-phenylpropane" and insert --2,2-bis-4(acryloxybisethylene glycol)-phenylpropane--.

Signed and Sealed this

Twenty-seventh Day of November, 2007

JON W. DUDAS
*Director of the United States Patent and Trademark Office*